United States Patent
Lee

(10) Patent No.: US 10,864,111 B2
(45) Date of Patent: Dec. 15, 2020

(54) TECHNIQUE FOR THERAPEUTIC CONTACT LENS SYSTEMS

(71) Applicant: Purdue Research Foundation, West Lafayette, IN (US)

(72) Inventor: Chi Hwan Lee, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 658 days.

(21) Appl. No.: 15/463,471

(22) Filed: Mar. 20, 2017

(65) Prior Publication Data

US 2017/0273731 A1 Sep. 28, 2017

Related U.S. Application Data

(60) Provisional application No. 62/311,867, filed on Mar. 22, 2016.

(51) Int. Cl.
*A61F 7/00* (2006.01)
*H04B 5/00* (2006.01)

(52) U.S. Cl.
CPC ............. *A61F 7/007* (2013.01); *A61F 7/00* (2013.01); *A61F 2007/0004* (2013.01); *A61F 2007/0071* (2013.01); *A61F 2007/0086* (2013.01); *A61F 2007/0095* (2013.01); *H04B 5/0037* (2013.01)

(58) Field of Classification Search
CPC .......... A61B 5/6821; A61F 2007/0071; A61F 9/00772
See application file for complete search history.

(56) References Cited

U.S. PATENT DOCUMENTS

| | | | | |
|---|---|---|---|---|
| 3,485,244 A | * | 12/1969 | Rosen | A61F 9/00 424/429 |
| 8,096,654 B2 | * | 1/2012 | Amirparviz | B29D 11/00826 345/8 |
| 8,446,341 B2 | * | 5/2013 | Amirparviz | A61B 5/1455 250/221 |
| 8,663,206 B2 | * | 3/2014 | Schachar | A61F 2/14 128/898 |
| 8,815,707 B2 | | 8/2014 | Lee et al. | |
| 8,945,101 B2 | * | 2/2015 | Herekar | A61F 9/00821 606/4 |
| 9,445,870 B2 | * | 9/2016 | Chuck | A61F 9/0079 |
| 9,977,256 B2 | * | 5/2018 | Pugh | G02C 7/022 |
| 2013/0211389 A1 | * | 8/2013 | Chuck | A61F 9/0079 606/5 |
| 2014/0379054 A1 | * | 12/2014 | Cooper | A61F 9/0079 607/90 |
| 2017/0071790 A1 | * | 3/2017 | Grenon | A61F 7/007 |

(Continued)

OTHER PUBLICATIONS

Alam et al., "Damage Tolerance in Naturally Compliant Structures", International Journal of Damage Mechanics, vol. 14, Oct. 2005, pp. 365-384.

(Continued)

*Primary Examiner* — Kaitlyn E Smith
(74) *Attorney, Agent, or Firm* — Mark S. Cohen; Pearl Cohen Zedek Latzer Baratz LLP

(57) ABSTRACT

The invention relates to electronic contact lens systems, methods for fabrication thereof, and uses thereof for treatment of ophthalmic diseases and conditions, for example, meibomian gland dysfunction.

10 Claims, 10 Drawing Sheets

(56) References Cited

U.S. PATENT DOCUMENTS

2018/0169905 A1* 6/2018 Marullo .......... B29D 11/00038
2019/0350699 A1* 11/2019 Jorgensen .............. G02C 7/083

OTHER PUBLICATIONS

Jung et al., "Highly Efficient Flexible Optoelectronic Devices Using Metal Nanowire-Conducting Polymer Composite Transparent Electrode", Electron. Mater. Lett., vol. 11, No. 5, Sep. 2015, pp. 906-914.

Lee et al., "Highly Stretchable and Highly Conductive Metal Electrode by Very Long Metal Nanowire Percolation Network", Adv. Mater., 2012, 24, pp. 3326-3332.

Liao et al., "A 3-µW CMOS Glucose Sensor for Wireless Contact-Lens Tear Glucose Monitoring", IEEE Journal of Solid-State Circuits, vol. 47, No. 1, Jan. 2012, pp. 335-344.

Lingley et al., "A single-pixel wireless contact lens display", Journal of Micromechanics and Microengineering, 21, Nov. 2011, 125014, 8 pages.

Nicolson et al., "Soft contact lens polymers: an evolution", Biomaterials 22 (2001) 3273-3283.

* cited by examiner

Figure 5A (left) Figure 5B (middle) Figure 5C (right)

Figure 6A (left) and Figure 6B (right)

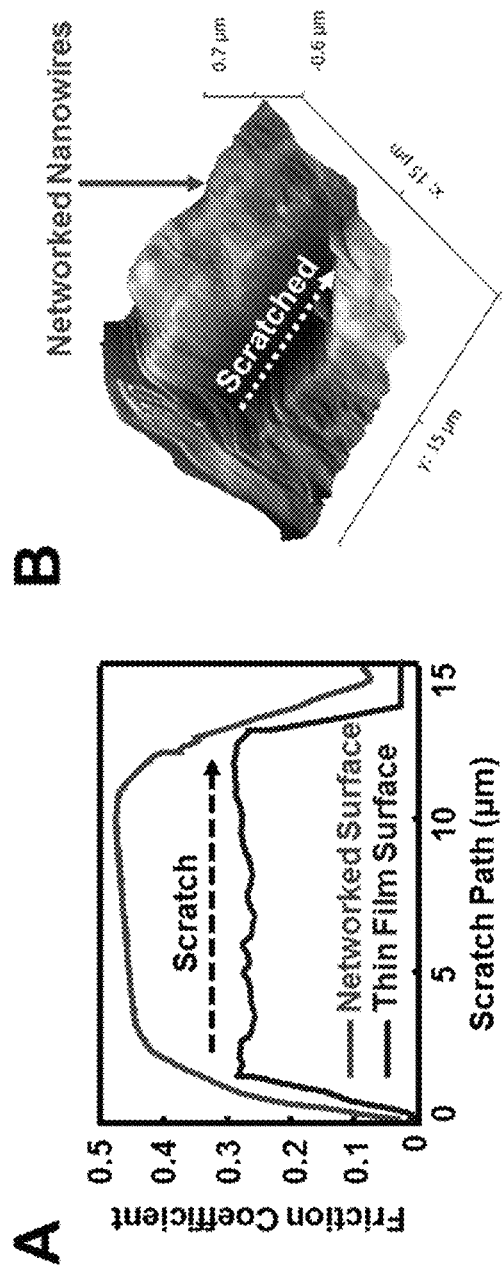
Figure 9A (left) and Figure 9B (right)

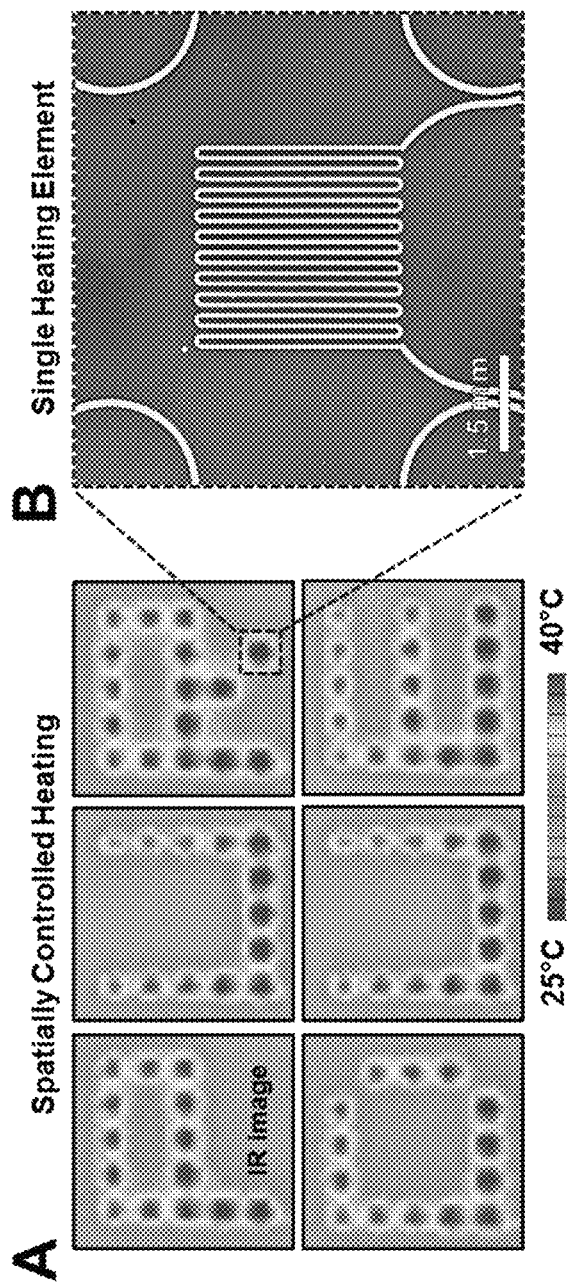
Figure 10A (left) and Figure 10B (right)

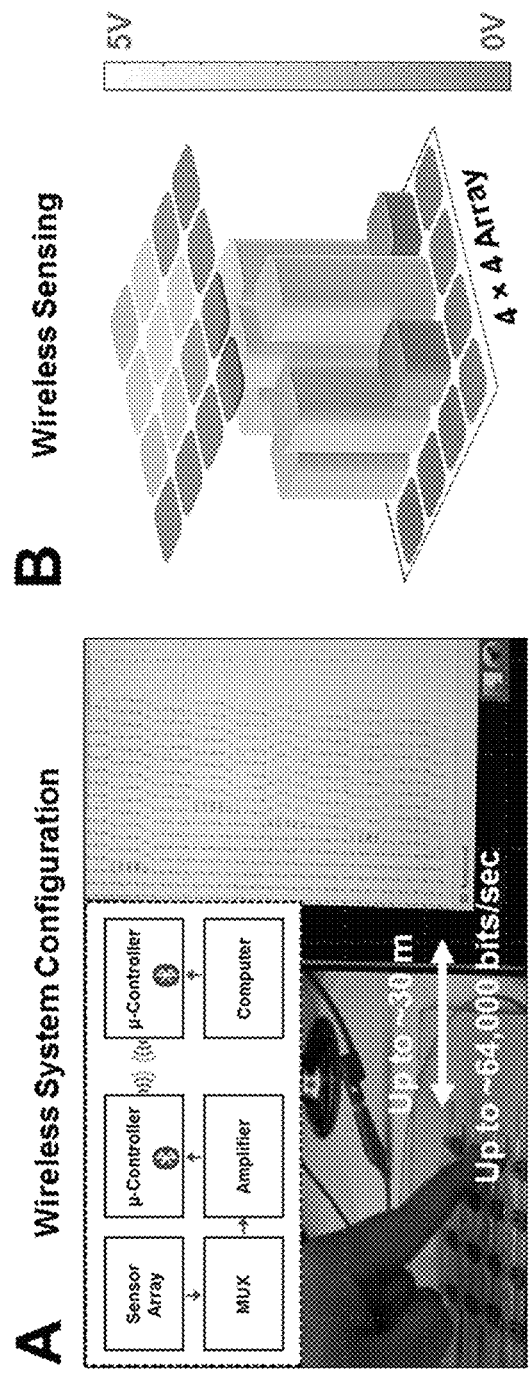
Figure 11A (left) and Figure 11B (right)

TECHNIQUE FOR THERAPEUTIC CONTACT LENS SYSTEMS

CROSS REFERENCE TO RELATED APPLICATIONS

This application claims the benefit of U.S. Provisional Application Ser. No. 62/311,867, filed on Mar. 22, 2016, which is incorporated herein by reference in its entirety.

TECHNICAL FIELD

This invention relates to electronic contact lens systems, methods for fabrication thereof, and uses thereof for treatment of ophthalmic diseases and conditions, for example, meibomian gland dysfunction.

BACKGROUND

Contact lenses have served mainly to correct vision problems. There exists great interest in using the lenses as medical devices with broad applications, such as relief of ocular pain, promotion of corneal healing, maintenance of corneal epithelial hydration, and drug delivery. Contact lenses offer a ubiquitous device platform for therapeutic ocular systems owing to their commercial availability, soft mechanics, ease of use, and ability to allow oxygen to pass through to the cornea (breathability).

Hard (plastic-based) contact lenses have served as a device platform to assemble functional electronic chips that act as chemical or pressure sensors. However, they are limited by poor biocompatibility and low oxygen permeability (breathability) (Liao, et al. *IEEE Journal of Solid State Circuits*, 2012, 47(1), 335-344; and Lingley, et al. *Journal of Micromechanics and Microengineering*, 2011, 21(12)).

Soft (silicone hydrogel-based) contact lenses offer a high degree of biocompatibility, wettability, and are approved for extended wear (up to ~30 days) (Nicolson, et al. *Biomaterials*, 2001, 22(24), 3273-3283). These factors make them an ideal platform for general use. But there is severe incompatibility between the soft, semielliptical surface of contact lenses and conventional semiconductor processing, which can only be applied to rigid, planar substrates. There is an on-going need to develop a novel fabrication technology to construct industry-grade electronics on the semielliptical surface of commercial soft contact lenses, thereby offering the necessary biocompatibility, comfortability, breathability, and long-term wearability.

SUMMARY OF THE INVENTION

In one aspect, the invention provides a method for fabricating an electronic contact lens, the method comprising
a) providing a thin film structure comprising a device layer on a support layer in an aqueous medium, wherein said device layer comprises electronic components and is encapsulated by a protection layer;
b) positioning a contact lens underneath the thin film structure in the medium; and
c) affixing the thin film structure to the contact lens by removing the medium.

In some embodiments, the thin film structure of the method of the invention is prepared by a method comprising
a) providing a substrate including a base and an oxide layer disposed over the base;
b) forming a metal layer over the oxide layer;
c) forming the support layer over the metal layer;
d) forming the device layer over the support layer, followed by adding the protection layer over the device layer to encapsulate the device layer;
e) performing an environment-assisted interfacial debonding to separate the device layer, the support layer, and the metal layer from the substrate; and
f) removing the metal layer from the encapsulated device layer and the support layer to produce the thin film structure.

In another aspect, the invention provides an electronic contact lens fabricated by the method of the invention.

In yet another aspect, the invention provides an electronic contact lens comprising a heating element, a sensing element, a wireless power supplier, and a transparent supporting/encapsulating layer, wherein said heating element is an independently, wirelessly addressable Joule heating resistor, wherein said sensing element is an array of temperature monitors based on pn-doped silicon nanomembranes, and wherein said wireless power supplier is an inductive coupled receiver coil connected to the heating element.

In yet another aspect, the invention provides a method of using an electronic contact lens of the invention, the method comprising a step of activating the electronic contact lens at a time by exploiting an electromagnetic field generator in a handheld hardware, wherein said activating triggers the heating element to generate heat consistently at a temperature during a prescribed treatment time.

In a further aspect, the invention provides a kit for treating an ophthalmic disease or condition in a subject, the kit comprising an electronic contact lens of the invention and a portable hardware unit, wherein said portable hardware unit comprises an electromagnetic field generator that can trigger the heating element of the electronic contact lens to generate heat at a temperature. In some embodiments, the portable hardware unit is a built-in wireless unit, such as a smartphone.

In a further aspect, the invention provides a method for treating an ophthalmic disease or condition in a subject, the method comprising placing an electronic contact lens of the invention over the eye of the subject in need thereof, followed by activating the electronic contact lens at a prescribed treatment time.

The details of one or more embodiments of the invention are set forth in the accompanying the description below. Other features, objects, and advantages of the invention will be apparent from the description and drawings, and from the claims.

Figure 5:
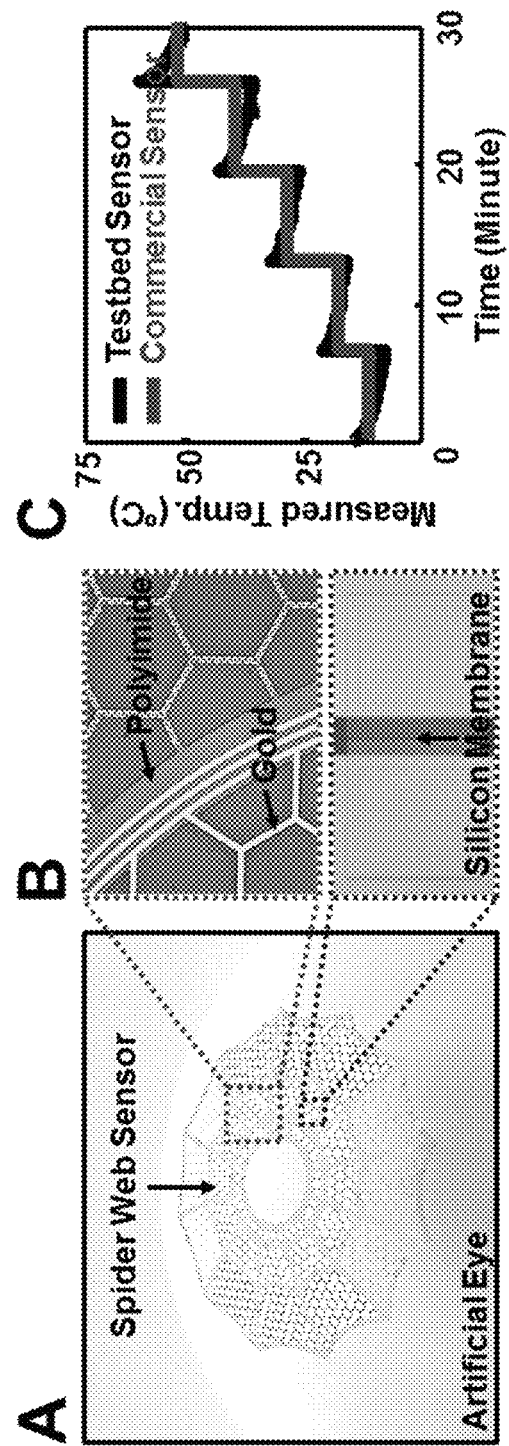
FIGS. 5A, 5B, and 5C depict an optical image of a testbed temperature sensor that is successfully constructed on an artificial eyeball (inset shows the embedded pn-doped silicon membrane (150 nm thick) for the high precision sensing element) (FIG. 5A); enlarged optical images of electrodes (gold), supporting/encapsulating layer (polyimide), and sensing element (pn-doped silicon membrane) (FIG. 5B)

and results of measured temperatures obtained by a testbed sensor (black line) and a commercial infrared (IR) camera (red line) (FIG. 5C).

Figure 6:
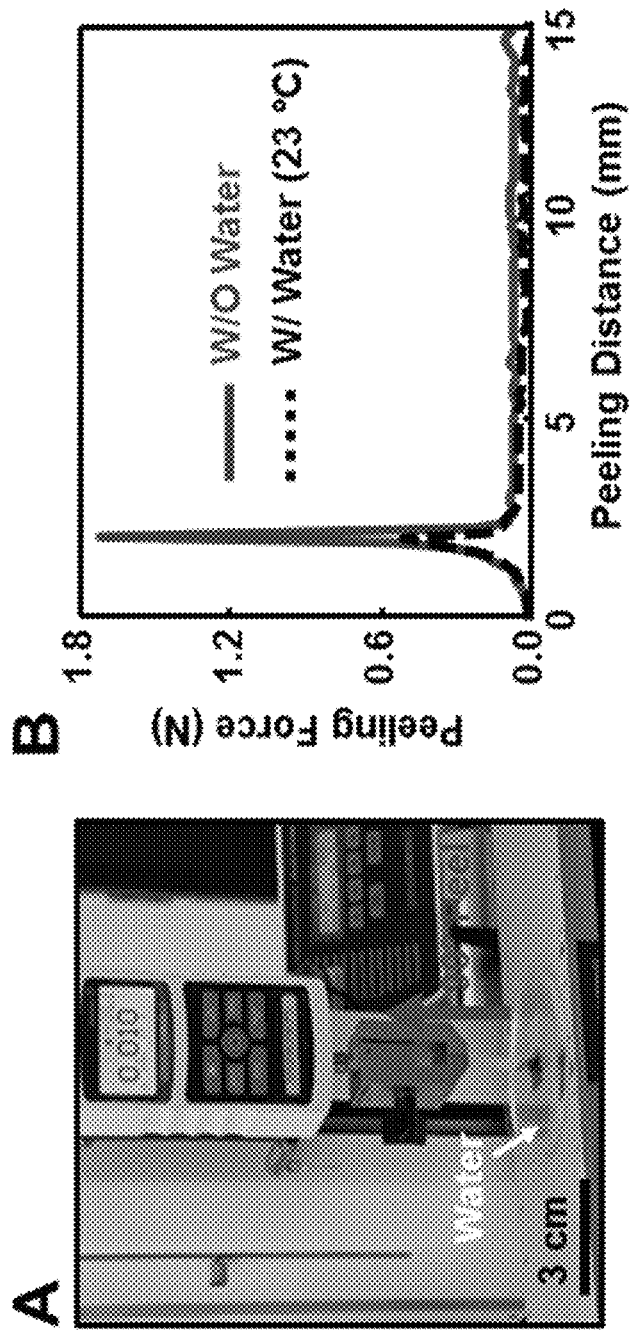

FIGS. 6A and 6B depict an experimental setup and representative preliminary results for studying the underlying mechanism of the transfer printing technique. FIG. 6A: an optical image of the experimental setup that allows to apply and measure peeling forces with a high precision in variously varied environments; and FIG. 6B: representative measurement results of peeling forces during the mechanical peeling process of a test sample with and without the presence of water at room temperature.

Figure 7:
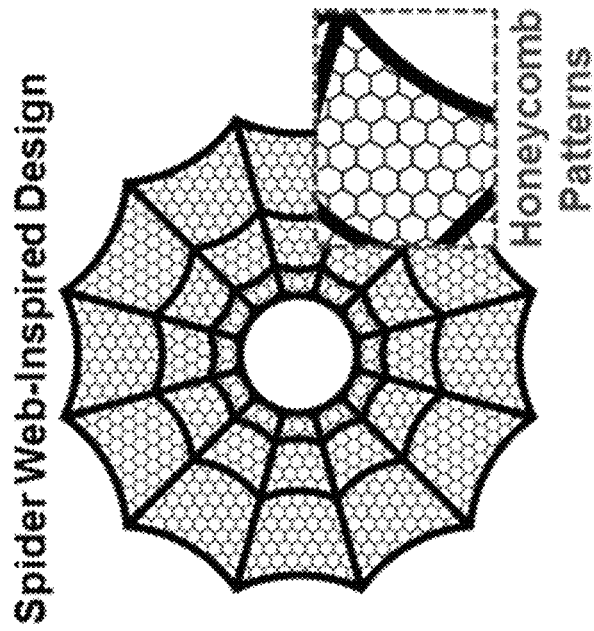

FIG. 7 depicts an example of spider web-inspired design that is combined with honeycomb patterns inside (inset).

Figure 8:
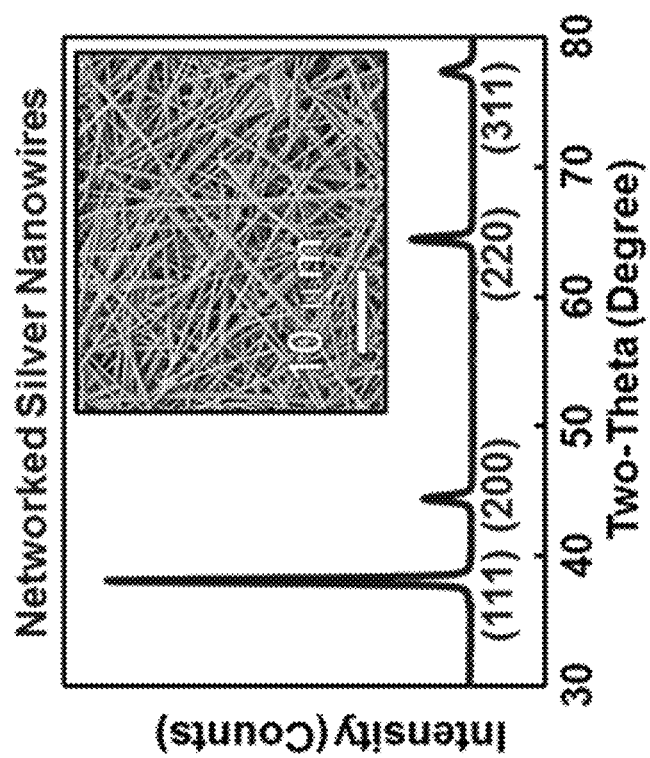

FIG. 8 depicts experimental results of XRD analysis and SEM image (inset) of highly networked silver nanowires.

FIGS. 9A and 9B depict results of a scratch test performed on the surfaces of a networked nanowires (red line) and a control thin film (blue line) (FIG. 9A) and a corresponding atomic force microscopy (AFM) image of the scratched surface of the networked nanowires (FIG. 9B).

FIGS. 10A and 10B depict a series of infrared (IR) images of the spatially controlled heating elements to present the "PURDUE" in a programmable fashion (FIG. 10A); and an optical image of a single Joule heating element used in the preliminary experiments (FIG. 10B).

FIGS. 11A and 11B depict an optical image of a wireless communication unit that sends the measured data from a 4×4 array of commercial pressure sensors to an external computer in a real-time fashion at a rate of 64,000 bits/sec (inset shows a block diagram of the arrangement of each component) (FIG. 11A); and three-dimensional view of wirelessly transmitted data of measured pressures by applying force (~10 g) on the top right corner of the sensor (FIG. 11B).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In one aspect, the invention provides a method for fabricating an electronic contact lens, the method comprising
d) providing a thin film structure comprising a device layer on a support layer in an aqueous medium, wherein said device layer comprises electronic components and is encapsulated by a protection layer;
e) positioning a contact lens underneath the thin film structure in the medium; and
f) affixing the thin film structure to the contact lens by removing the medium.

In some embodiments, the medium is water. In other embodiments, the media is a saline solution. In some embodiments, the saline solution is normal saline solution that has a pH of 7 and a NaCl concentration of ~0.9% w/v.

In some embodiments, the electronic components comprises a heating element, a sensing element, and a wireless power supplier;

In some embodiments, the distance between the thin film structure and the contact lens underneath the thin film structure is from about 2 mm to about 6 mm. In other embodiments, the distance between the thin film structure and the contact lens underneath the thin film structure is from about 3 mm to about 5 mm. For example, the distance between the thin film structure and the contact lens underneath the thin film structure is about 3 mm, or about 4 mm, or about 5 mm.

In some embodiments, the contact lens is a soft contact lens that is commercially available.

In some embodiments, the device layer is designed in a way to form a stretchable pattern inspired by spider webs. In some embodiments, the device layer is designed in a way to form a stretchable pattern inspired by spider webs such that the electronic components are embedded in the spider web patterns and the open mesh area would be empty. In some embodiments, the open mesh area may include additional electronic components. In some embodiments, the electronic components are transparent and mechanically soft. In some embodiments, the term "mechanical softness" or "mechanically soft" as used herein refers to that the entire thin film structure including the electronic components is mechanically flexible and compliant to the surface of the contact lens to which it is attached. In some embodiments, the material for the electronic components is nanomaterials. In some embodiments, the material for the electronic components is silver nanowires, carbon nanotubes, graphene, or a combination thereof. In certain embodiments, the material for the electronic components is silver nanowires.

In another aspect, the present invention provides a method for fabricating an electronic contact lens, the method comprising
a) providing a thin film structure comprising a stack of device layers on a support layer in a solution;
b) positioning a contact lens underneath the thin film structure in the solution with a distance of from about 2 mm to about 6 mm; and
c) affixing the thin film structure to the contact lens by removing the solution.

In some embodiments, the stack of device layers is encapsulated in a protection layer.

In some embodiments, the solution is water or a saline solution.

In some embodiments, the distance between the thin film structure and the contact lens underneath the thin film structure is from about 3 mm to about 5 mm.

In some embodiments, the method of the invention further comprises a step of stretching the thin film structure prior to affixing the thin film structure to the contact lens. In some embodiments, the thin film structure is stretched uniaxially more than 30%.

In some embodiments, the method of the invention further comprises a step of bending the thin film structure prior to affixing the thin film structure to the contact lens.

The method of the invention uses a soft contact lens as a device platform to construct high-performance semiconductor devices on three-dimensional surfaces of diverse soft materials. For example, a silicone hydrogel-based contact lens can be used as an ergonomic platform.

In some embodiments, the soft contact lens is commercially available soft contact lenses that comprise an ophthalmically compatible, three-dimensional cast molded material having an equilibrium water content of at least ~40% by weight and considerably low mechanical modulus (0.5~1.0 MPa).

The integration of a two-dimensional thin film structure onto a three-dimensional (semielliptical) contact lens requires precise mechanical design to accommodate the mechanical mismatch from their geometric discrepancy. In the method of the invention, mechanics theories such as mechanical isolation strategies are applied. The method of the invention allows the thin film structure to be efficiently stretched and bent during integration with contact lenses. Analytical mechanics modeling, such as finite element modeling (FEM), can be developed to give insight into the mechanical behavior of the structure and the optimal design of the system.

In some embodiments, to precisely position an ultrathin device structure afloat on the surface of the medium (e.g., water or saline solutions) at the exact location of target soft contact-lens, a micro XYZ positioning stage equipped with a charge-coupled device (CCD) camera and microscope can be built on an anti-vibration table to ensure the continuous, real-time monitoring of the device floating on the medium. A high-resolution linear DC motor with a controller can be used for linear displacement of the ultrathin device afloat. The grips at the tips of the manipulators can be coated with a thin layer of polydimethylsiloxane (PDMS) to ensure solid contact through van der Waals adhesions and to prevent scratching the surface of ultrathin device by the mechanical contacts. The contact lens can be fixed underneath the medium surface by a distance of approximately 3~5 mm to the device. Once the ultrathin device structure or layer and soft contact lens are positioned properly, a certain quantity of the medium can be carefully removed from the container to make physical contact between the aligned device and the contact lens underneath.

The thin film structure in the method of the invention can be prepared by the methods known in the art, for example, by the method disclosed in U.S. Pat. No. 8,815,707, the disclosure of which is hereby incorporated herein by its entirety. In some embodiments, the thin film structure in the method of the invention is prepared by a method comprising
  g) providing a substrate including a base and an oxide layer disposed over the base;
  h) forming a metal layer over the oxide layer;
  i) forming the support layer over the metal layer;
  j) forming the device layer over the support layer, followed by adding the protection layer over the device layer to encapsulate the device layer;
  k) performing an environment-assisted interfacial debonding to separate the device layer, the support layer, and the metal layer from the substrate; and
  l) removing the metal layer from the encapsulated device layer and the support layer to produce the thin film structure.

In some embodiments, the base is a silicon base. In other embodiments, the oxide layer is a silicon oxide. In some embodiments, the silicon oxide is silicon dioxide. In some embodiments, the base is a silicon base and the oxide layer is a silicon oxide.

In some embodiments, the metal layer comprises at least one metal selected from nickel and copper. In certain embodiments, the metal layer comprises copper.

In some embodiments, the environment-assisted interfacial debonding is an aqueous solution-assisted interfacial debonding. In some embodiments, the environment-assisted interfacial debonding is a saline solution-assisted interfacial debonding. For example, the saline solution is normal saline solution that has a pH of 7 and a NaCl concentration of ~0.9% w/v. In other embodiments, the environment-assisted interfacial debonding is a water-assisted interfacial debonding.

In some embodiments, the support layer is a polymer layer. In certain embodiments, the polymer is hydrogel, polyimide, or silbione. In some embodiments, the polymer is hydrogel. In other embodiments, the polymer is polyimide. In certain embodiments, the polymer is a silicone-based elastomer, for example, silbione.

In the method of the invention, the thin film structure can also be prepared by the method comprising
  a) providing a substrate including a base and an oxide layer disposed over the base;
  b) forming a metal layer over the oxide layer;
  c) forming the support layer over the metal layer
  d) forming a stack of device layers over a support layer;
  e) performing water-assisted interfacial debonding of the metal layer to separate the stack of device layers, the support layer, and the metal from the substrate; and
  f) removing the metal layer from the stack of device layers and the support layer.

In some embodiments, the base is a silicon base. In some embodiments, the oxide layer is a silicon oxide. In some embodiments, the silicon oxide is silicon dioxide. In other embodiments, the metal layer includes at least one metal selected from nickel and copper.

In some embodiments, the support layer is a polymer layer. In some embodiments, the polymer for the polymer layer is polyimide or polydimethylsiloxane.

In some embodiments, the support layer has a thickness of from about 1 µm to about 10 µm. In other embodiments, the support layer has a thickness of from about 1 µm to about 4 µm, or from about 1 µm to about 6 µm, or from about 1 µm to about 8 µm. In some embodiments, the support layer has a thickness of from about 4 µm to about 10 µm, or from about 6 µm to about 10 µm, or from about 8 µm to about 10 µm. In certain embodiments, the support layer has a thickness of from about 4 µm to about 8 µm or from about 4 µm to about 6 µm.

In some embodiments, the method for preparing the thin film layer further comprises a step of forming a protection layer encapsulating the stack of devices layers prior to performing water-assisted interfacial debonding.

In some embodiments, the step of performing water-assisted interfacial debonding is carried out at a temperature in a range of from 10° C. to 30° C. In some embodiments, the temperature is about 15° C. In other embodiments, the temperature is 20° C. or 25° C.

In some embodiments, the method of the invention includes the following basic steps. A fabrication substrate (e.g., silicon wafer) is used to build completely integrated electronics on (to form a thin device layer) by traditional techniques such as photolithographic patterning, depositions, and etchings. The entire structure is then immersed in a medium, for example, water or a commercial saline solution, at room temperature, followed by a mechanical delamination of the thin device layer (typically <3 µm thick) from the fabrication substrate (e.g., the silicon wafer) by exploiting an automatic peeling tool (LT-111, MicroTestMachines Inc., Peeling velocity: ~0.1 mm/min). The molecular reactions involved at the delamination interface, referred to as the environment-assisted subcritical debonding in classical fracture mechanics, allow facilitating intact interfacial debonding of the thin device layer or stacked thin film layers from the fabrication substrate.

The medium, e.g., a commercial saline solution, provides reactive ions that can furthermore facilitate the molecular reactions for the debonding process and simultaneously offer excellent compatibility with any kinds of soft contact lenses. The separated device layer is integrated onto a soft contact lens by using XYZ-type micromanipulators. The ultralow mechanical modulus of such thin device layer allows the formation of highly conformal contacts onto the curvilinear surface of a soft contact lens. The novel transfer printing technique of the present invention can physically separate the completed electronics from the fabrication silicon wafer and then integrating onto a range of commercial soft contact lenses. The technique is suitable for the three-dimensional (3D), soft, and wet surface of soft contact lenses by exploiting aqueous solutions such as commercial saline solutions or water as a fabrication mean.

In another aspect, the method of the invention features an optimized mechanics to accommodate the mechanical strains associated with semielliptical surface of contact lenses. The fabrication method also provides important features of the underlying materials and mechanics and design rules for general types of three-dimensional electronics. The method of the invention circumvents the limitation associated with the incompatibility issues between existing semiconductor device processing and unusual substrates that do not tolerate the processing conditions, such as high temperatures, chemicals, and pressures.

It is another aspect of the invention that an electronic contact lens can be fabricated by the method of the invention as described herein. In some embodiments, the electronic contact lens of the invention comprises a heating element, a sensing element, a wireless power supplier, and a transparent supporting/encapsulating layer.

In some embodiments, the invention provides an electronic contact lens comprising a device layer, wherein the device layer comprises a heating element, a sensing element, a wireless power supplier, and a transparent supporting/encapsulating layer.

In some embodiments, in the electronic contact lens of the invention, the heating element is an independently, wirelessly addressable Joule heating resistor; the sensing element is an array of temperature monitors based on pn-doped silicon nanomembranes; and the wireless power supplier is an inductive coupled receiver coil connected to the heating element. In some embodiments, the transparent supporting/encapsulating layer is a layer of ultrathin biocompatible materials.

In some embodiments, the heating element comprises transparent and flexible conductors. In some embodiments, the heating element is located in the center areas of the contact lens. In some embodiments, the heating element comprises transparent and flexible conductors and the heating element is located in the center areas of the contact lens. In some embodiments, the heating element is a metallic nanomaterial. In certain embodiments, the heating element is a copper nanowire or a silver nanowire. In other embodiments, the heating element is a gold nanowire.

In some embodiments, the sensing element is evenly distributed over the entire areas of the contact lens.

In some embodiments, the inductive coil comprises a thin conducting film. In some embodiments, the inductive coil is located at the peripheral areas of the contact lens in a circular path. In some embodiments, the inductive coil comprises a thin conducting film and the inductive coil is located at the peripheral areas of the contact lens in a circular path. In some embodiments, the inductive coil is a magnetic inductive coupling coil or an inductive charging coil. In some embodiments, the thin conducting film is a copper thin film.

In some embodiments, the electronic contact lens of the invention further comprises a built-in wireless unit located around the peripheral areas of the contact lens. The built-in wireless unit comprises a wireless data communication element, a micro-controller, and a programmable input/output peripheral. In certain embodiments, the wireless unit has a thickness of less than 1 mm. In some embodiments, the wireless unit has a weight of less than 2 grams.

It is another aspect of the present invention that the electronic soft contact lens as described herein includes a wirelessly addressable heating element that offer the ability to provide electronically controlled heat. The embedded functionality by exploiting internal temperature sensors can monitor the local temperature distributions over the heating surfaces, thereby eliminating the risk of thermal damage onto the cornea, eyelid, tear film and contact lens. A fully miniaturized unit of wireless system for energy harvesting and data communications can be monolithically integrated, allowing the user-friendly operation by a portable hardware unit such as a smartphone.

In some embodiments, the method of the invention as described herein can be used for fabrication of a therapeutic contact lens system that combines semiconducting nanomaterials and metallic/insulating traces to serve as 1) a thermal actuator (Joule heating resistor), 2) a wireless power supplier, and 3) an array of silicon-based temperature sensors. All of these components can be embedded in a commercially available soft contact lens in stretchable formats suitable for the semielliptical surface of contact lenses. Such contact lens system is able to provide controlled heat to safely melt the obstructed secretions with internal temperature sensors eliminating the risk of thermal damage. It will be appreciated by persons skilled in the art that the method and the electronic contact lens of the invention can be applied to methods, materials, and design concepts for broad applications in ocular clinical practices.

In some embodiments, the terms "therapeutic contact lens," "thermal therapeutic contact lens," and "electronic contact lens" are used interchangeably herein.

In a further aspect, the therapeutic contact lens of the invention comprises a wirelessly addressable thermal actuator having a resistive heating element, an inductively coupled receiver coil system connected to the heating element, and an array of temperature sensors. In some embodiments, the resistive heating element is activated remotely with a power transmitter. In some embodiments, said resistive heating element is located in the center of the contact lens. In some embodiments, the resistive heating element is a metallic nanomaterial. In certain embodiments, said metallic nanomaterial is a copper nanowire or a silver nanowire. In some embodiments, the array of temperature sensors monitors the surface temperature of inner eyelids.

It is another aspect of the invention that the thermal therapeutic contact lens system of the invention uses specially designed induction coils as a wireless power receiver for which a commercially available wireless inductive charger that typically uses an induction coil to create an alternating electromagnetic field, which can deliver power to the system. This configuration can allow home remedy applications for sustained relief from dry eye syndrome.

In some embodiments, the thermal therapeutic contact lens system of the invention includes 1) an independent, wirelessly addressable thermal actuator (Joule heating resistor), 2) an inductive coupled receiver coil connected to the resistive heating element for a wireless power supplier, and 3) an array of temperature monitors for thermal mapping on the surface of inner eyelids; all built on a commercially available soft contact lens. The heaters on a soft contact lens are activated remotely with a handheld power transmitter, enabling the contact lenses to induce constant temperatures directly to the surface of the inner eyelids while the temperature sensors monitor the surface of the inner eyelids to eliminate the risk of thermal damage.

To avoid blocking the wearer's view through the contact lens, optical transparency of the resistive (Joule) heating elements can be located in the center (vision area) of the contact lens. For example, one-dimensional metallic nanomaterials can be used. For example, copper or silver nanowires can be used in the thermal therapeutic contact lens system due to their excellent transparency and inexpensiveness. The one-dimensional nanowires allow electrical percolation networks, enabling steady conductivity under deformations. The thermal therapeutic contact lens system of the invention can also provide a rich interface between nanomaterials and ocular organs from sensing to action, and ultimately provide a basic platform for scientific studies of the ocular system at the nanoscale.

The electronic contact lens of the invention requires the ability to withstand diverse mechanical deformation modes including bending, stretching, and compressing induced by the natural behaviors of wearer. The integration of 2D thin film electronics onto 3D surface (semielliptical) of soft contact lenses demands precise mechanics design to efficiently accommodate the induced strains from the mechanical mismatch. Further, optical transparency of the constituent electronic materials is highly necessary to secure the wearer's vision. Thus, optimal designs and materials to achieve the mechanical stability and optical transparency are needed.

There are several classic mechanics theories that allow mechanically isolating the system from the bending and stretching. Neutral mechanical plane (NMP) allows the device layer to experience no stresses during the bending by compensating the strains in the above and below areas. Several forms of serpentine layouts can be used to accommodate most of the strain effectively under stretching. Sophisticated analytical mechanics modeling by exploiting a finite element analysis (FEA) may provide insight into the mechanical behavior of the device and feedback to establish optimal designs.

Several stretchable design layouts (e.g., serpentine filamentary) can be applied to the device layer to efficiently accommodate the induced mechanical strains during the integration between 2D thin films and 3D soft contact lens. Laminating a thin layer of transparent, breathable material such as hydrogel, polyimide, and silbione can form an encapsulation layer not only to secure the mechanical bonding but also protect the embedded electronic elements from the environments. Industry-grade single crystalline silicon membranes can serve as the active semiconducting components for all the various devices.

In the electronic contact lens of the invention, the device layer is designed in a way to form a spider web-inspired structural pattern, which is a naturally evolved, elegant architecture capable of efficiently resisting various mechanical loads from environments. For an instance, spider webs are resilient enough to withstand harsh mechanical loads such as showers and even storms. In addition, the geometries include excellent "damage-tolerance" in which the spider webs are still functional to catch prey in spite of several cut threads (Alam, et al. *International Journal of Damage Mechanics* 14, 365-384 (2005)). Such electronic soft contact lens has several unique features. For example, the spider web-inspired design layouts are capable of efficiently distributing the induced stresses throughout the threads depending on the effective ratio of radial and spiral dimensions. The hierarchical web patterns induce the principle attributes of "damage-tolerance" in which the entire structure can retain its strength and function properly in spite of minor cut threads. The fractal web patterns enable unusually compliant mechanics to support the mechanical deformations under tension. These physical attributes are highly desirable for the electronic soft contact lenses, allowing to efficiently accommodate the induced mechanical strains during both the fabrication process and the natural behaviors of wearers such as blinking, rubbing, pressing, and/or scratching.

The significantly increased surface area by exploiting the highly networked nanowires can improve the Van der Waals adhesion force to the substrate. For example, the correlation between surface roughness and contact adhesion can be determined by exploiting a T-peeling tester equipped with a high-resolution force gauge (Mark-10, Copiague, N.Y., Resolution: ±0.25%). Chemical or optical treatments for the surface functionalization can be exploited if further enhanced bonding adhesion is required. Moreover, the representative functionalities such as mobility, conductivity, and sensitivity of the devices can be monitored while applying the various mechanical deformation forces such as pressing, rubbing, and scratching. The computational modeling (FEA) then reveals the underlying mechanics under the various loading conditions to determine whether the maximum principle stresses/strains reach the fracture limits of the constituent electronic components.

It is another aspect of the invention that the electronic contact lens is used in a method for treating an ophthalmic disease or condition in a subject, wherein the method comprises placing an electronic contact lens of the invention over the eye of the subject in need thereof, followed by activating the electronic contact lens at a prescribed treatment time. In some embodiments, the prescribed treatment time is about 10 minutes, or about 11 minutes, or about 12 minutes, or about 13 minutes, or about 14 minutes, or about 15 minutes. In other embodiments, the treatment time is prescribed based on the severity of the diseases or conditions.

The obstructive meibomian gland dysfunctions (MGDs) can serve as a model system to demonstrate the utility of the electronic soft contact lenses of the invention in chronic eye care. The MGDs are the most common form of lid margin diseases that are considered a prime suspect in the dry eye syndrome, eyelid inflammation, hypersecretion and abnormal excreta of the meibomian glands. The primary cause of the MGDs involves the chronically clogged obstructions in the meibomian gland, eventually preventing the secretion of oil into the tear film. Traditional treatments exploit home-based warm compresses in forms of towels moistened with hot water, face-masks and goggles for which the heat (40~43° C.) distributes onto the external eyelid, allowing to melt the clogged obstructions in the meibomian gland. The clogged obstructions are largely based on oil in which the melting temperature (32~40° C.) lies below the maximum allowable temperature (~45° C. for >~35 min of uninterrupted exposure) to the corneas and eyelid tissues before thermal damage. Thus, it is another aspect of the invention that the electronic contact lens is used in a method for treating an ophthalmic disease or condition in a subject. In some embodiments, the ophthalmic disease or condition is meibomian gland dysfunction.

The comprehensive system of the invention can form a basis to adapt broad types of therapeutic contact lens systems for eye care applications. For example, the therapeutic contact lens system can be used to treat meibomian gland dysfunction (dry eye syndrome), which is caused by chronically clogged meibomian glands, in which secrete oils prevent tears from quickly evaporating. The therapeutic contact lens system of the invention would enable to provide controlled temperatures to melt the clogged secretions (melting temperatures: 32° C. to 45° C.) so that internal temperature sensors eliminate the risk of thermal damage. Accordingly, the therapeutic contact lens system of the invention can monitor the level of ocular infections and remotely provide treatments. The development of this technology can significantly advance ocular biomedical devices for use in the treatment of eye diseases and conditions.

The electronic contact lens of the invention can be easily operated and activated at a prescribed treatment time by exploiting the electromagnetic field generators in a handheld hardware. The activating triggers the heating element to generate heat consistently at a temperature during the prescribed treatment time. In some embodiments, the temperature is about a temperature from 38° C. to about 42° C. In certain embodiments, the temperature is about 40° C. In some embodiments, the prescribed treatment time is about 10 minutes, or about 11 minutes, or about 12 minutes, or about 13 minutes, or about 14 minutes, or about 15 minutes. In other embodiments, the duration of treatment is prescribed based on the severity of the diseases or conditions.

In yet another aspect, the invention provides a kit for treating an ophthalmic disease or condition in a subject, wherein the kit comprises an electronic contact lens of the invention and a portable hardware unit, wherein said portable hardware unit comprises an electromagnetic field generator that can trigger the heating element of the electronic contact lens to generate heat at a temperature. In some embodiments, the portable hardware unit is a built-in wireless unit, such as a smartphone. In some embodiments, the temperature is about a temperature from 38° C. to about 42° C. In certain embodiments, the temperature is about 40° C. In some embodiments, the prescribed treatment time is about 10 minutes, or about 11 minutes, or about 12 minutes, or about 13 minutes, or about 14 minutes, or about 15 minutes. In other embodiments, the treatment time is prescribed based on the severity of the diseases or conditions.

The electronic contact lens of the invention is significantly advanced and superior over the traditional methodologies for the treatment of an ophthalmic disease or condition. It is capable of providing uniform/constant temperature in an electronically controlled fashion directly onto the inner eyelid where meibomian glands are located. The electronic contact lens can include additional units for wireless data communication, powering, and control systems, thereby enabling autonomous operation with confirmed biosafety. The electronic contact lens of the invention can provide a basis for more diverse types of therapeutic soft contact lenses that can offer tailored treatment regimens according to the monitored level of diseases.

The invention will be further illustrated with reference to the following illustrative examples, which are not intended to limit the scope of the invention in any manner.

EXAMPLES

Example 1: Separation of Thin Film Structures from Fabrication Substrate

The separation of thin film structures (the functional device) from the silicon fabrication wafer can be achieved through controlled delamination and then floating the thin film structure on the surface of water. The high surface tension of water can provide an ideal temporary support during the integration of the thin film structure and the contact lens.

Figure 1:
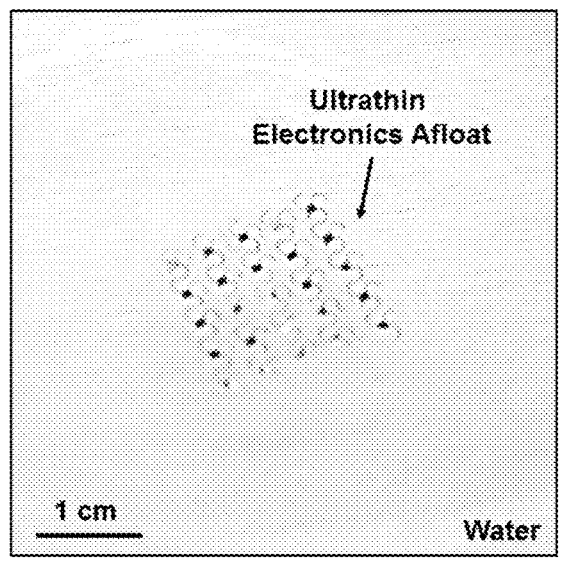
FIG. 1 depicts an ultrathin test structure on water.
Figure 2:
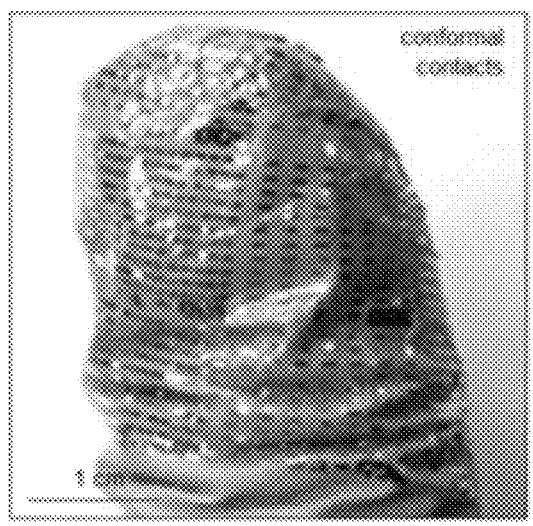
FIG. 2 depicts an ultrathin test structure on a gloved fingertip.

FIG. 1 presents a preliminary example by exploiting a simplified test structure (1 μm thick) that was separated from a fabrication wafer and then released on water. The ultrathin specimen was kept afloat easily and slides frictionlessly on the surface of water. The extremely low mechanical modulus of the ultrathin specimen was also wrapped around a gloved fingertip (FIG. 2).

Example 2: Stretching and Bending

The mechanical transformation of the two-dimensional thin film structure into a three dimensional shape involves deformation modes in stretching and bending. For the stretching mode, the 'device-islands/serpentine-interconnector' design, which is widely applied in stretchable electronics owing to its ability to control strains under stretching, can be adopted. The mechanically isolated device-island, which includes sophisticated electronics components, can withstand negligible strain while the serpentine elastic interconnectors accommodate most of the strain.

Figure 3:
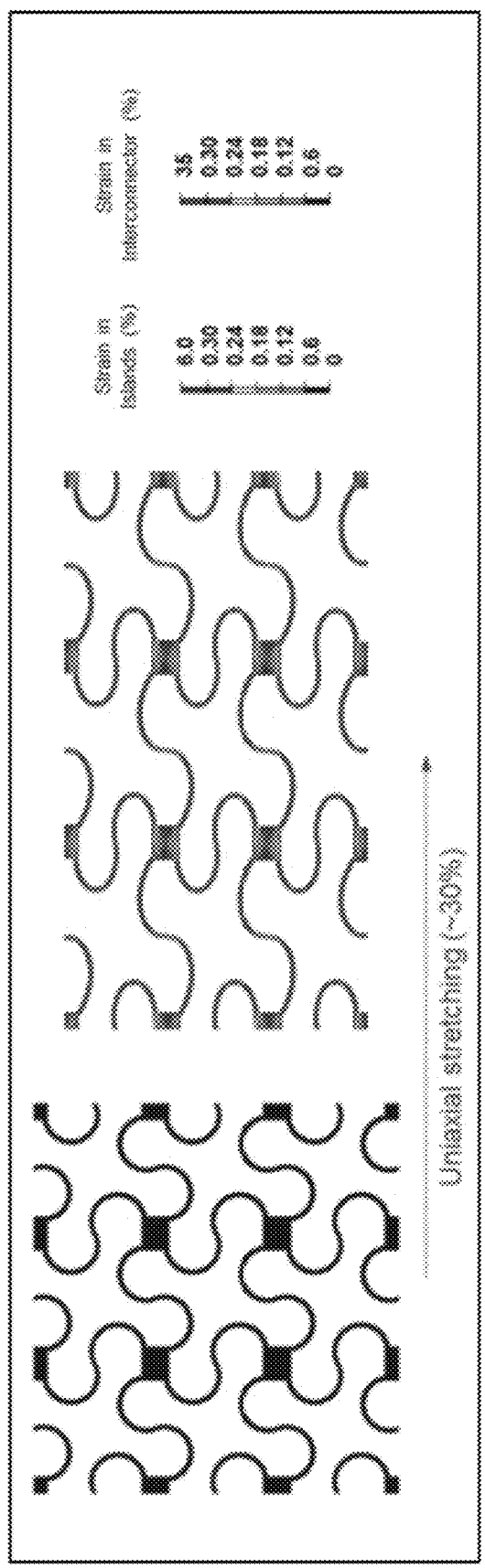
FIG. 3 depicts preliminary Finite Element Modeling (FEM) results of a test structure with the device-islands/serpentine-interconnector design under uniaxial stretching.

FIG. 3 shows preliminary results of an FEM analysis by exploiting a simplified test structure that comprises the device-island/serpentine interconnector design. When stretched uniaxially up to 30%, the device-islands exhibited little stress whereas the serpentine-interconnectors accommodate stress effectively.

For the bending mode, a classical mechanics theory, such as neutral mechanical plane, can be used. The active device layer can be placed on the mechanically neutral plane to minimize strains when bent. For instance, when the thin film structure is bent down, the top surface is in tension and the bottom surface is in compression to compensate the strains on each other, and therefore the middle surface is not under any strain (neutral plane). A layer of encapsulation which materials and geometries are sophisticatedly designed can be used to place the electronics components at the neutral mechanical plane. These design layouts can exhibit a linear, elastic mechanical response over a large range of deformations from stretching and bending during the integration process of the thin film structure and the contact lens. Various choices of topologies ranging from lines to loops and to branch-like meshes can be applied with focus on the linear, elastic mechanical responses over the range of geometric transformations on semielliptical shapes.

Example 3: Planispiral Design

Figure 4:
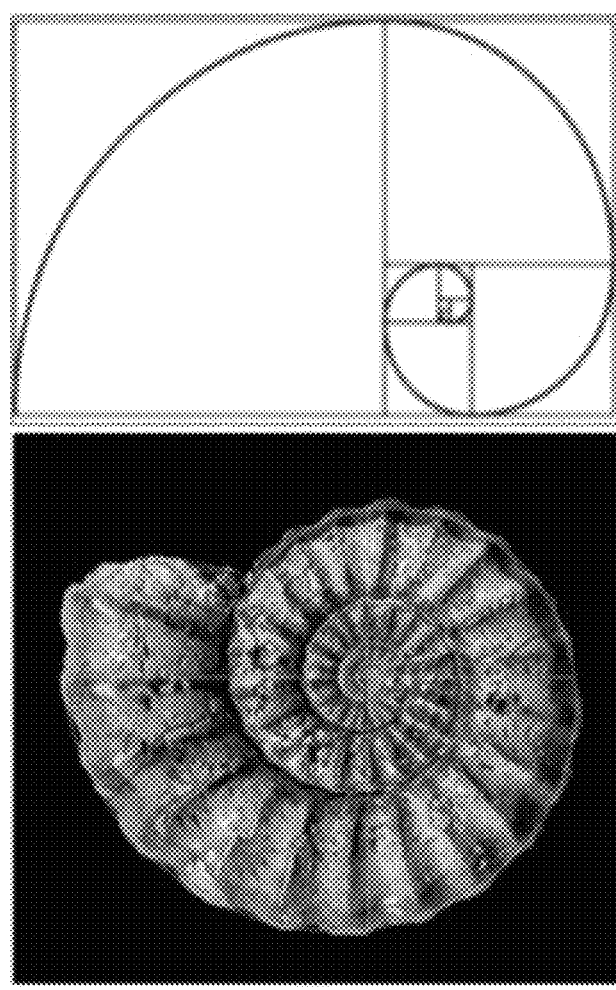
FIG. 4 depicts an example design of fractal geometries inspired by an Ammonite shell.

To avoid mechanical failure on the edges where the highest stresses are concentrated, the device designs can exploit nature-inspired fractal geometries. An example is the planispiral pattern adopted from the Ammonite shell (FIG. 4), which is well known as a nearly perfect logarithmic spiral with a regular ribbing pattern. This has important consequences for mechanical force generated during growth leading to tissue-scale morphogenesis. The underlying mechanics of this approach can reap the benefits of these fractal-based designs, which accommodate enhanced elastic strain around the curvilinear surface of contact lenses and support biaxial, radial and other deformation modes.

Example 4: Construction of Electronics onto Curved Surface

FIG. 5A shows a preliminary data of a testbed temperature sensor that was successfully transferred onto the curved surface (~3 cm dia.) of an artificial eyeball (made of silicone elastomer). As shown in the enlarged images (FIG. 5B), the testbed sensor consists of gold (200 nm thick), elastomeric polyimide (1.5 μm thick), and pn-doped silicon membrane (150 nm thick) to serve as the conducting electrodes, supporting/encapsulating layer, and sensing element, respectively. FIG. 5C (black line) shows representative results of the measured temperature by varying environmental temperature ranging from room temperature to 50° C. in a stepwise manner with the sensitivity of ~1.82 mV/° C. This result shows minimal differences by comparison to those obtained from a commercial infrared (IR) camera (FLIR SC645, Sensitivity: 0.05° C., red line), demonstrating the industry-grade performances of the proposed devices.

Example 5: Controlled Peeling

Chemical reactions involved between saline molecules and strained crack-tip atomic bonds, as well as the reaction kinetics, are sensitive to pH, temperature and the addition of stabilizing surfactants in the water. The optimum aqueous chemistries can be determined by systematically studying the role of temperature, applied loads, pH, and added surfactants.

As shown in FIG. 6A, the experimental setup includes a mechanical T-peeling tester equipped with a high-resolution force gauge (Mark-10, Copiague, N.Y., Resolution: ±0.25%), allowing to precisely apply normal peeling forces in the manipulated environments (i.e., with and without water, different solutions, temperatures, surfactants, etc). Representative results obtained from this setup are provided in FIG. 6B, proving that the initial peeling force without water is significantly higher than counterpart with presence of water at room temperature, which are consistent with the experimental observations. Various choices of materials with varied thicknesses for the interface and aqueous solutions can be also applied.

Example 6: Spider Web Design

FIG. 7 shows an example of the device layer design that mimics the planar orb webs of the garden spider *Araneus diadematus*, consisting of fractal motifs with the engineered ratio of forces in radii and mooring threads of 1:7. The basic structure includes honeycomb-like patterns (inset), allowing to provide not only the wide open mesh spaces for the placement of electronic elements but also the capability of being efficiently stretched to accommodate additional mechanical strains. The force can be selectively distributed throughout the structure depending on the number of spiral thread, radial spacing between adjacent nodes, and side length of honeycomb's hexagonal holes.

Various structural designs of arbitrary geometries can also be applied by observing the time-dependent stress-strain behaviors. A computational modeling such as finite element analysis (FEA) can be employed to understand the dynamic behaviors of candidate designs, thereby revealing the underlying principle strains.

Example 7: Electronic Materials

The electronic materials for the electronic contact lenses require both optical transparency and mechanical softness to avoid obstructed vision of wearers and achieve comfortable wearability, respectively. Various nanomaterials such as silver nanowires, carbon nanotubes, graphene, and a combination thereof can serve as the transparent, flexible conductors. For example, highly-networked silver nanowires have well proven for their excellent mechanical flexibility, optical transparency, and electrical conductivity (Jung, et al. *Electronic Materials Letters* 11, 906-914 (2015) and Lee, et al. *Advanced Materials* 24, 3326-3332 (2012)).

FIG. 8 provides the experimental results of X-ray diffraction analysis (XRD; Normal Powder X-ray Diffractometer; RIGAKU, D/MAX-2500, ~40 kV, ~300 mA) for a representative highly-networked silver nanowires prepared by exploiting traditional vacuum-filtration methods. The results indicate the single crystalline structures of the networked silver nanowires where the diffraction peaks imply the cubic forms of the silver. The inset shows an optical image of the as-prepared networked silver nanowires with average lengths of ~50 μm. The sheet resistance is considerably low within below ~10 $\Omega \cdot sq^{-1}$ with an optical transparency of ~65%, establishing a good starting point for implementing further optimizations in the proposed work. For the supporting/encapsulating layers, several materials such as hydrogel, polyimide, and silbione can be used due to their already-proven biocompatible, flexibility, and transparency.

Example 8: Mechanical and Electrical Stability

Mechanical/electrical stability of the electronic contact lens system is critical not only to reliably maintain the encoded functionalities but also to secure the safety of wearers. The excessive shear stress is the primary factor that leads to the undesirable delamination of the constituent components. A nanoindentation tester (Hysitron, TI950 TriboIndentor) can be employed for scratching a diamond tip across the surface of the testbed contact lens systems. This experimental setup can record the exerted forces and displacements to the surface in shear direction, leading to the qualitative evaluations of tribological properties.

A representative preliminary data were collected in FIGS. 9A and 9B by scratching the diamond tip across the surface of the networked nanowires and a control planar thin film. The results show that the friction coefficient, defined as the ratio of lateral force ($F_L$) to normal force ($F_N$), for the surface of the networked nanowires (red line) experiences minor fluctuations at around 0.45 which is ~60% higher than that for the surface of the control thin film (blue line). Corresponding surface topography for the networked nanowires, obtained from an atomic force microscopy (AFM, Asylum research, MFP-3D), is provided in FIG. 9B, showing a clear scratch mark left behind on the surface. The deviations in the friction coefficients indicate how the scratched surface changes tribological properties, thereby providing important feedback for design improvements that allow the electronic components to maintain functionalities against the inadvertent scratching by wearers.

Example 9: Electronic Soft Contact Lens Systems

The electronic soft contact lens system includes (1) an independent, wirelessly addressable Joule heating resistor to serve as a heater, (2) an array of temperature monitors based on pn-doped silicon nanomembranes to serve as a sensing element, (3) an inductive coupled receiver coil connected to the resistive heating elements to serve as a wireless power supplier, and (4) ultrathin biocompatible materials to serve as a transparent supporting/encapsulating layer, all built on a commercially available soft contact lens. The testbed system can take multilayer configurations in which the locations of each component are as follow: (1) The heater that includes the transparent/flexible conductors can take the center areas of the contact lens exactly where meibomian glands are located with eyes closed, (2) The temperature sensing elements can be evenly distributed over the entire areas of the contact lens so that the array of sensors can map the thermal distributions in a spatially controlled manner, (3)

The inductive coils that include a thin conducting film can take the most peripheral areas of the contact lens in a circular path, and (4) An ultrathin layer of biocompatible materials as described herein can serve as a supporting/encapsulation layer for all the electronic components to promote biocompatibility, comfortability, and adhesions.

Example 10: Operations/Activations

The wearer activates the electronic contact lens at prescribed time (twice a day for 12 minutes over 6 months) by exploiting the already embedded electromagnetic filed generators in a commercial handheld hardware (i.e., smartphone) in which their impedances are matched well. The activation triggers the embedded heating elements to generate heat consistently at ~40° C. during the prescribed treatment time (~12 minutes) while the eyes are closed.

Preliminary results are provided in FIG. 10A for a series of infrared (IR) images of the selectively activated 5×5 array of Joule heating elements, demonstrating the ability to apply highly localized heat in a spatially controlled manner by presenting the "PURDUE" in a programmable fashion. The temperature increases are linearly proportional to the incident power, thereby allowing controlled operation to reliably maintain the target temperature by time. An optical image of a single Joule heating element is provided in FIG. 10B. The temperature sensing elements by exploiting the pn-doped silicon membranes can be also incorporated for simultaneous mapping of thermal distributions over the heating area, allowing not only to record the history of thermal application by time but also to detect any over-heating accidents. Additional built-in wireless unit of a microcontroller connected with a switching component can be included for autonomous controls and/or shutdowns as described herein.

Example 11: Built-In Wireless Unit

A built-in wireless unit can offer real-time data communications and autonomous controls of the therapeutic heat. The miniaturizations of necessary electronic components for the wireless unit can first be achieved; thereby can prevent any uncomfortable sensation. The components can include (1) a Bluetooth antenna (Pulse, W3008, 2.4 GHz, 1 mm thick) that serves as wireless data communications from/to a smartphone, (2) A 32-bit ARM Cortex M0 processor based micro-controller (Nordic, NRF51822, 500 µm thick) containing the main processor core, non-volatile Electrically Erasable Programmable Read-Only Memory (EEROM), and (3) programmable input/output peripherals that enables the autonomous controls of entire system. These components can be located around peripheral areas of the contact lens to avoid disrupting the wearer's view where the ultralow modulus silicone elastomer (Silbione RT Gel 4717, Bluestar Silicones, USA) seamlessly encapsulates the entire unit to secure the comfort and safety. The estimated maximum thickness and weight of the wireless unit are within <~1 mm thick and <~2 g, respectively.

Arrangements of these components can also allow continuously recording the applied heat measured by the sensors and then wirelessly send the data to an external data acquisition hardware such as a smartphone. Such monitoring mechanism enables to provide real-time data of medically useful information such as the history of heat applied directly onto the cornea during the treatments. The embedded microcontroller can provide the ability to immediately shut down the entire system whenever overheating accident is detected, thereby eliminating the potential risk of thermal damages. The heating elements can be controlled by varying the duty cycle of a square wave with a switching frequency and duty cycle of ~490 Hz and 4 milliseconds (shutdown time), respectively.

FIG. 11A presents a preliminary data for a wireless unit that exploits a 4×4 array of commercial pressure sensors that are capable of wirelessly sending the measured data to an external computer in a real-time fashion at a rate of 64,000 bits per second and up to a distance of 30 meters. Post-processed data of the measured pressure by pressing (~10 g) on the top right corner of the sensor array appears in FIG. 11B in a three-dimensional view. These components and arrangements can be used in the electronic contact lens of the invention.

Example 12: In Vivo Evaluations

In vivo evaluations can be conducted on a white rabbit model that has served as the standard species for the inspection of conventional contact lenses. At least 30 adult white rabbits can be used in the evaluations. The rabbits can be housed individually and allowed food and water ad libitum. All procedures can conform to the guidelines set forth by NIH and be approved by the Animal Care and Use Committee at Purdue University. The rabbits can be placed into a cylindrical fixation device without anesthetic. The testbed contact lens system can be carefully worn on the cornea of rabbits.

First, for the access of biocompatibility and long-term wearability, the rabbits can be observed up to more than 3 weeks by frequently examining the eyes at intervals of 3 hours for any abnormal findings such as inflammation responses.

Second, for the access of functionality, the testbed system can be activated wirelessly twice a day to apply constant heat at 40° C. for 12 minutes. The local temperature can be monitored over the heated areas by exploiting the embedded sensors in a continuous fashion while simultaneously monitor the temperature is monitored by using a commercial IR camera (FLIR SC645, sensitivity: 0.05° C.) to confirm that no overheating accident occurs. It can be examined and verified if the applied heat is tolerable and safe for the cornea, eyelid, tear film, and soft contact lens.

Third, for the access of mechanical stability, the physical conditions of the testbed system can be inspected at regular intervals of ~3 hours to evaluate the sustainability against the natural behaviors of the rabbits such as blinking, rubbing, pressing, and scratching.

Finally, for the access of bioefficacy in clinical trials, the rabbits with obstructive meibomian gland dysfunction can be selected. The meibomian gland dysfunction can be induced in at least 20 rabbits by applying 2% epinephrine twice daily for a period of 6 months while the eye lids are being observed by exploiting an immunofluorescent microscopy. The treatment regime can include the daily (twice) applications of controlled heating at 40° C. for 12 minutes using the testbed system. The 1-month and 1-year post-treatment status of the subjects can be determined by measuring the meibomian gland function, tear break-up time, and dry eye symptoms. At least 7 age-matched rabbits can serve as controls and be randomly assigned to the conventional warm compress applications that exploit a hot towel (40~43° C.) for 12~15 minutes onto the external eyelids with reheating every 2 minutes.

Those skilled in the art will recognize that numerous modifications can be made to the specific implementations described above. The implementations should not be limited to the particular limitations described. Other implementations may be possible.

What is claimed is:

1. An electronic contact lens comprising a heating element, a sensing element, a wireless power supplier, and a transparent supporting/encapsulating layer, wherein said heating element is an independently, wirelessly addressable Joule heating resistor, wherein said sensing element is pn-doped silicon nanomembranes, and wherein said wireless power supplier is an inductive coupled receiver coil connected to the heating element.

2. The electronic contact lens of claim 1, wherein said heating element is transparent and flexible conductors and wherein the heating element is located in the center areas of the contact lens.

3. The electronic contact lens of claim 2, wherein said conductors are metallic nanowires.

4. The electronic contact lens of claim 1, wherein said sensing element is evenly distributed over the entire areas of the contact lens.

5. The electronic contact lens of claim 1, wherein said inductive coil comprises a thin conducting film and wherein the inductive coil is located at the peripheral areas of the contact lens in a circular path.

6. The electronic contact lens of claim 5, wherein said inductive coil is a magnetic inductive coupling coil or an inductive charging coil.

7. A method of using the electronic contact lens of claim 1, the method comprising a step of activating the electronic contact lens at a time by exploiting an electromagnetic field generator in a handheld hardware, wherein said activating triggers the heating element to generate heat consistently at a temperature during a prescribed treatment time.

8. A kit for treating an ophthalmic disease or condition in a subject, the kit comprising an electronic contact lens of claim 1 and a portable hardware unit, wherein said portable hardware unit comprises an electromagnetic field generator that can trigger the heating element of the electronic contact lens to generate heat at a temperature.

9. A method for treating an ophthalmic disease or condition in a subject, the method comprising placing an electronic contact lens of claim 1 over the eye of the subject in need thereof, followed by activating the electronic contact lens at a prescribed treatment time.

10. The method of claim 9, wherein said ophthalmic disease or condition is meibomian gland dysfunction.

* * * * *